US011253488B2

(12) United States Patent
Howard et al.

(10) Patent No.: US 11,253,488 B2
(45) Date of Patent: Feb. 22, 2022

(54) SUBLINGUAL EPINEPHRINE TABLETS

(71) Applicant: pHase Pharmaceuticals LLC, Dallas, TX (US)

(72) Inventors: G. Lynn Howard, Dallas, TX (US); Nicholas J. Farina, Solebury, PA (US); Edward J. Walters, Allentown, NJ (US); Christopher Howard, Dallas, TX (US)

(73) Assignee: pHase Pharmaceuticals LLC, Dallas, TX (US)

( * ) Notice: Subject to any disclaimer, the term of this patent is extended or adjusted under 35 U.S.C. 154(b) by 0 days.

(21) Appl. No.: 16/114,939

(22) Filed: Aug. 28, 2018

(65) Prior Publication Data

US 2019/0070131 A1 Mar. 7, 2019

Related U.S. Application Data

(60) Provisional application No. 62/554,979, filed on Sep. 6, 2017.

(51) Int. Cl.
| | | |
|---|---|---|
| *A61K 31/137* | (2006.01) | |
| *A61K 9/00* | (2006.01) | |
| *A61K 9/20* | (2006.01) | |
| *A61P 3/08* | (2006.01) | |
| *A61K 47/26* | (2006.01) | |
| *A61K 47/38* | (2006.01) | |
| *A61P 37/08* | (2006.01) | |
| *A61K 47/12* | (2006.01) | |

(52) U.S. Cl.
CPC ............ *A61K 31/137* (2013.01); *A61K 9/006* (2013.01); *A61K 9/2018* (2013.01); *A61K 9/2054* (2013.01); *A61K 47/12* (2013.01); *A61K 47/26* (2013.01); *A61K 47/38* (2013.01); *A61P 3/08* (2018.01); *A61P 37/08* (2018.01)

(58) Field of Classification Search
CPC ...... A61K 31/137; A61K 47/12; A61K 47/38; A61K 47/26; A61K 9/2054; A61K 9/2018; A61K 9/006; A61P 37/08; A61P 3/08

See application file for complete search history.

(56) References Cited

U.S. PATENT DOCUMENTS

| | | | |
|---|---|---|---|
| 2007/0059361 A1* | 3/2007 | Rawas-Qalaji | A61K 9/0056 424/464 |
| 2007/0202163 A1 | 8/2007 | Rawas-Qalaji et al. | |
| 2007/0293580 A1 | 12/2007 | Hill | |
| 2007/0293581 A1 | 12/2007 | Hill | |
| 2007/0293582 A1 | 12/2007 | Hill | |
| 2008/0269347 A1* | 10/2008 | Bruss | A61P 37/08 514/653 |
| 2010/0240631 A1* | 9/2010 | Bellorini | A61K 9/0056 514/177 |
| 2012/0322884 A1 | 12/2012 | Rawas-Qalaji et al. | |
| 2014/0242177 A1 | 8/2014 | Rawas-Qalaji et al. | |
| 2015/0164827 A1 | 6/2015 | Rawas-Qalaji et al. | |
| 2016/0045457 A1 | 2/2016 | Rawas-Qalaji et al. | |
| 2017/0020827 A1* | 1/2017 | Rawas-Qalaji | A61K 31/137 |

FOREIGN PATENT DOCUMENTS

| | | |
|---|---|---|
| WO | WO-2007-143674 | 12/2007 |
| WO | WO-2007-143675 | 12/2007 |
| WO | WO-2007-143676 | 12/2007 |
| WO | WO-2011-109340 | 9/2011 |
| WO | WO-2013-059629 | 4/2013 |
| WO | WO-2014-007972 | 1/2014 |
| WO | WO-2014-153559 | 9/2014 |
| WO | WO-2015/034822 | 3/2015 |

OTHER PUBLICATIONS

Barsan et al., "A hemodynamic model for anaphylactic shock." Annals of Emergency Medicine, 1985; 14(9): pp. 834-839.
Chernoff et al., "Responses of the rat foetus to maternal injections of adrenaline and vasopressin," Br. J. Pharmacol., 1971; 43: pp. 270-278.
Dietz, D. NTP Technical Report on the Toxicology and Carcinogenesis Studies of I-Epinephrine Hydrochloride (CAS No. 55-31-2) in F344/N Rats and B6C3F1 Mice (Inhalation Studies). (1990) NTP TR 380. NIH Publication No. 90-2835. National Toxicology Program. Public Health Service. National Institutes of Health. U.S. Department of Health and Human Services.
EpiPen® [Prescribing Instructions]. (Feb. 2017). Basking Ridge, NJ: Mylan Specialty L.P.
Gold et al., "First aid anaphylaxis management in children who were prescribed an adrenaline autoinjector device (EpiPen)," Journal of Allergy and Clinical Immunology, 2000; 106(1 Pt 1): pp. 171-176.
Gu et al. "Is epinephrine administration by sublingual tablet feasible for the first-aid of anaphylaxis? A proof-of-concept study." Biopharm Drug Dispos, 2002; 23: pp. 213-216.
McNeil et al., "Accidental Digital Epinephrine Injection, to treat or not to treat?" Can Fam Physician., Aug. 2014; 60(8) : pp. 726-728.).
Product Label Epinephrine Injection, USP 0.3 mg/0.3 mL (Manufactured for Belcher Pharmaceuticals, LLC, Manufactured by Sintetica SA), Feb. 2017.
Pumphrey et al., "Postmortem findings after fatal anaphylactic reactions," J Clin Pathol, 2000; 53: pp. 273-276.
Pumphrey, "Lessons for management of anaphylaxis from a study of fatal reactions," ClinExp Allergy, 2000; 30: pp. 1144-1150.
Sampson et al., "Second symposium on the definition and management of anaphylaxis: Summary report—Second National Institute of Allergy and Infectious Disease/Food Allergy and Anaphylaxis Network symposium," Journal of Allergy and Clinical Immunology, Feb. 2006; 117(2): pp. 391-397.

(Continued)

*Primary Examiner* — Snigdha Maewall
(74) *Attorney, Agent, or Firm* — Arnall Golden Gregory LLP

(57) ABSTRACT

The present disclosure provides sublingual epinephrine tablets and methods of treating anaphylaxis, methods for concomitant therapy during a cardiac event, treating hypoglycemia, and prophylaxis for immunotherapy, using sublingual epinephrine tablets.

7 Claims, 6 Drawing Sheets

(56) References Cited

OTHER PUBLICATIONS

Simons al., "EpiPen Jr versus EpiPen in young children weighing 15 to 30 kg at risk for anaphylaxis," J Allergy Clin Immunol, 2002; 109:pp. 171-175.
Simons et al., "Epinephrine absorption in adults: Intramuscular versus subcutaneous injection," J Allergy Clin Immunol, 2001; 108: p. 871.
Simons et al., "Epinephrine absorption in children with a history of anaphylaxis," J Allergy Clin Immunol, 1998; 101: pp. 33-37.
Simons et al., "Sublingual epinephrine administration in humans: a preliminary study," J Allergy Clin Immunol Abstract, 2004; 938: p. S260.
Simons, "First-aid treatment of anaphylaxis to food: Focus on epinephrine," J Allergy Clin Immunol, 2004; 113(5): pp. 837-844.
Summary Basis of Approval for Auvi-Q™ Auto-Injector (Intelliject Inc.). U.S. Department of Health and Human Services, Food and Drug Administration, Center for Drug Evaluation and Research (CDER), NDA 201739, Aug. 2012.
Westfall et al., Chapter 10: Catecholamines, sympathetic drugs, and adrenergic receptor antagonists. (2005) in: Goodman and Gilman's The Pharmacological Basis of Therapeutics, 11th Ed. McGraw-Hill. New York, NY.
Kemp et al., "Epinephrine: The Drug of Choice for Anaphylaxis—A Statement of the World Allergy Organization," WAO Journal 2008; 2: pp. S18-S26.
Monsod et al., "Epipen as an Alternative to Glucagon in the Treatment of Hypoglycemia in Children with Diabetes," Diabetes Care, 2001; 24(4): pp. 701-704 (abstract).
Nolte et al., "Epinephrine Use in Clinical Trials of Sublingual Immunotherapy Tablets," J Allergy Clin Immunol Pract., 2017; 5(1): pp. 84-89 (abstract).
Prajapati et al., "Preparation and Evaluation of Sublingual Tablets of Zolmitriptan," International Journal of Pharmaceutical Investigation, 2014; 4(1): pp. 27-31.
Rachid et al., "Dissolution Testing of Sublingual Tablets: a Novel in Vitro Method" AAPS PharmSciTech, 2011; 12(2): pp. 544-552.
Rizava et al., "Antigen-Based Immunotherapies do not Prevent Progression of Recent-Onset Autoimmune Diabetes: A Systematic Review and Meta-Analysis," Endocrine, 2016; 54(3): pp. 620-633 (abstract).
International Search Report and Written Opinion issued in PCT/US18/48319, dated Nov. 26, 2018.

* cited by examiner

FIGURE 1

Main Study Dose Administration Details

| Animal Number | Group Number | Day of Dose | Total Horse Serum Challenge Volume (mL) | Baseline MAP (mmHg) | Epinephrine Treatment | Postdose MAP[a] (mmHg) | MAP Change from Baseline (mmHg) | Percent MAP Change (%) | Rescue Drugs? | Classification |
|---|---|---|---|---|---|---|---|---|---|---|
| 101 | 1 | 41 | 1.5 | 67 | Tablet (citrate) | 53 | 14 | 20.9 | No | Moderate Responder |
| 401 | 4 | 41 | 1.5 | 65 | Saline | 40 | 25 | 38.5 | Yes | Responder |
| 701 | 7 | 41 | NA | 48 | Injection | NA | NA | NA | No | NA |
| 702 | 7 | 41 | NA | NA[b] | NA[b] | NA[b] | NA[b] | NA[b] | Yes[b] | NA[b] |
| 703 | 7 | 41 | NA | 63 | Injection | NA | NA | NA | No | NA |
| 301 | 3 | 42 | 2 | 62 | Tablet (citrate) | 44 | 18 | 29.0 | No | Responder |
| 302 | 3 | 42 | 2 | 61 | Tablet (no citrate) | 23 | 38 | 62.3 | No | Responder |
| 303 | 3 | 42 | 2 | 69 | Injection | 52 | 17 | 24.6 | No | Non-Responder |
| 304 | 3 | 42 | 2 | 50 | Tablet (citrate) | 49 | 1 | 2.0 | No | Non-Responder |
| 305 | 3 | 42 | 2 | 55 | Tablet (no citrate) | 23 | 32 | 58.2 | Yes | Responder[c] |
| 402 | 4 | 42 | 2 | 62 | Injection | 55 | 7 | 11.3 | No | Non-Responder |
| 201 | 2 | 43 | 1 | 54 | Tablet (citrate) | 14 | 40 | 74.1 | Yes | Responder |
| 202 | 2 | 43 | 1 | 58 | Tablet (no citrate) | 14 | 44 | 75.9 | Yes | Responder |
| 203 | 2 | 43 | 0.5 | 60 | Tablet (citrate) | 26 | 34 | 56.7 | No | Responder |
| 204 | 2 | 43 | 1 | 69 | Tablet (no citrate) | 57 | 12 | 17.4 | No | Moderate Responder |
| 205 | 2 | 43 | 2 | 67 | Tablet (no citrate) | 61 | 6 | 9.0 | No | Non-Responder |
| 206 | 2 | 43 | 2 | 72 | Tablet (no citrate) | 57 | 15 | 20.8 | No | Responder |
| 102 | 1 | 44 | 1 | 61 | Tablet (no citrate) | 49 | 12 | 19.7 | No | Moderate Responder |
| 103 | 1 | 44 | 1 | 61 | Injection | 40 | 21 | 34.4 | No | Responder |
| 104 | 1 | 44 | 2 | 82 | Injection | 47 | 35 | 42.7 | No | Responder |
| 105 | 1 | 44 | 2 | 77 | Tablet (citrate) | 77 | 0 | 0.0 | No | Non-Responder |
| 106 | 1 | 44 | 0.5 | 60 | Tablet (citrate) | 40 | 20 | 33.3 | No | Responder |
| 306 | 3 | 44 | 1 | 63 | Tablet (no citrate) | 43 | 20 | 31.7 | No | Responder |

[a] The reported MAP was the lowest reading taken either just prior to epinephrine injection, immediately after injection, or the next reading taken immediately after injection.
[b] Animal died during surgery
[c] Animal died after 10 minutes postdose
NA – Not applicable

FIGURE 2

| Dose (mg) | Route | Treatment | Statistic | $C_{max}$ (ng/mL) | $C_{max}$/Dose (kg*ng/mL/mg) | $T_{max}^{a}$ (min) | $T_{last}^{a}$ (min) | $AUC_{0-60min}$ (min*ng/mL) | $AUC_{0-60min}$/Dose (min*kg*ng/mL/mg) | Relative Bioavailability[b] |
|---|---|---|---|---|---|---|---|---|---|---|
| 35 (citrate and no citrate)[c] | Buccal | Induced Anaphylaxis | N | 14 | 14 | 14 | 14 | 13 | 13 | NA |
| | | | Mean | 41.1 | 1.18 | NA | 60 | 900 | 25.7 | 2.81 |
| | | | SD | 27.0 | 0.772 | (2 - 60) | (10 - 60) | 695 | 19.9 | NA |
| | | | CV% | 65.6 | 65.6 | NA | NA | 77.3 | 77.3 | NA |
| 0.30[d] | Intramuscular | Induced/Non-Induced Anaphylaxis | N | 5 | 5 | 5 | 5 | 5 | 5 | NA |
| | | | Mean | 7.84 | 26.1 | 7.5 | 60 | 274 | 913 | NA |
| | | | SD | 3.62 | 12.1 | (2 - 60) | (60 - 60) | 138 | 461 | NA |
| | | | CV% | 46.2 | 46.2 | NA | NA | 50.5 | 50.5 | NA |
| 0 (Placebo) | Intramuscular | Induced Anaphylaxis | N | 1 | NA | 1 | 1 | 1 | NA | NA |
| | | | Mean | 6.96 | NA | 10 | 60 | 246 | NA | NA |
| | | | SD | NA | NA | NA | NA | NA | NA | NA |
| | | | CV% | NA | NA | NA | NA | NA | NA | NA |

NA - Not applicable
SD and CV are not calculated or not reported when N < 3
a: Median (minimum - maximum), median value only reported if actual collection interval
b: Relative Bioavailability (expressed as a percent) = [AUC/Dose $_{Buccal (Citrate\ and\ No\ Citrate\ Combined)}$]/[AUC/Dose $_{IM\ (induced\ and\ non-induced\ combined)}$] * 100

FIGURE 3

| Dose (mg) | Route | Treatment | Day | Gender | Subject | Cmax (ng/mL) | Cmax/Dose (kg*ng/mL/mg) | Tmax (min) | Tlast (min) | AUCTlast (min*ng/mL) | AUC$_{0-60min}$ (min*ng/mL) | AUC$_{0-60min}$/Dose (min*kg*ng/mL/mg) |
|---|---|---|---|---|---|---|---|---|---|---|---|---|
| 35 (citrate) | Buccal | Induced Anaphylaxis | 1 | Male | 101 | 27.0 | 0.771 | 30 | 60 | 794 | 794 | 22.7 |
| | | | | Male | 105 | 60.7 | 1.73 | 60 | 60 | 2580 | 2580 | 73.6 |
| | | | | Male | 106 | 108 | 3.09 | 2 | 60 | 1360 | 1360 | 38.8 |
| | | | | Male | 201 | 10.5 | 0.300 | 2 | 60 | 417 | 417 | 11.9 |
| | | | | Male | 203 | 53.3 | 1.52 | 20 | 60 | 1300 | 1300 | 37.2 |
| | | | | Male | 301 | 15.9 | 0.454 | 15 | 60 | 347 | 347 | 9.91 |
| | | | | Male | 304 | 40.9 | 1.17 | 10 | 60 | 561 | 561 | 16.0 |
| 35 (no citrate) | Buccal | Induced Anaphylaxis | 1 | Male | 102 | 61.2 | 1.75 | 60 | 60 | 1180 | 1180 | 33.8 |
| | | | | Male | 202 | 52.5 | 1.50 | 15 | 60 | 1710 | 1710 | 48.9 |
| | | | | Male | 205 | 28.9 | 0.826 | 2 | 60 | 196 | 196 | 5.59 |
| | | | | Male | 206 | 8.96 | 0.256 | 2 | 60 | 354 | 354 | 10.1 |
| | | | | Male | 302 | 13.5 | 0.386 | 2 | 60 | 379 | 379 | 10.8 |
| | | | | Male | 305 | 56.0 | 1.60 | 5 | 10 | 330 | NA[a] | NA[a] |
| | | | | Male | 306 | 38.7 | 1.11 | 7.5 | 60 | 517 | 517 | 14.8 |
| 0.30 | Intramuscular | Induced Anaphylaxis | 1 | Male | 103 | 5.00 | 16.7 | 60 | 60 | 163 | 163 | 544 |
| | | | | Male | 104 | 14.0 | 46.7 | 60 | 60 | 498 | 498 | 1660 |
| | | | | Male | 303 | 6.43 | 21.4 | 5 | 60 | 292 | 292 | 973 |
| 0 (Placebo) | Intramuscular | Induced Anaphylaxis | 1 | Male | 401 | 6.96 | NA | 10 | 60 | 246 | 246 | NA |
| 0.30 | Intramuscular | Non-induced Anaphylaxis | 1 | Male | 701 | 5.73 | 19.1 | 7.5 | 60 | 157 | 157 | 524 |
| | | | | Male | 703 | 8.06 | 26.9 | 2 | 60 | 259 | 259 | 862 |

NA - Not applicable
a: AUC$_{0-60min}$ not reported due to early death following the 10 minute collection interval

FIGURE 4

5mg strength materials/concentrations

| | 5mg Stand-Alone Blend Formulation | | |
|---|---|---|---|
| Item No. | Ingredient | Concentration (%w/w) | mg/Dose |
| 1 | Epinephrine Bitartrate | 10.11 | 9.10 (5.00)[1] |
| 2 | Avicel PH 102 | 14.52 | 13.07 |
| 3 | Avicel PH105 | 3.82 | 3.44 |
| 4 | Ludiflash | 64.29 | 57.86 |
| 5 | Croscarmellose sodium | 5.00 | 4.50 |
| 6 | Citric acid, anhydrous | 1.26 | 1.13 |
| | Magnesium Stearate | 1.00 | 0.90 |
| | Total | 100.00 | 90.00 |

1* Conversion factor for Epinephrine Bitartrate to Epinephrine is 1.82 : 1.00

FIGURE 5

10mg, 15mg, 25mg strength common blend materials/concentrations

| | 10mg+15mg+25mg Common Blend Formulation | | | | |
|---|---|---|---|---|---|
| Item No. | Ingredient | Concentration (%w/w) | mg/Dose | mg/Dose | mg/Dose |
| 1 | Epinephrine Bitartrate | 20.22 | 18.20 (10) | 27.30 (15) | 45.50 (25)[1] |
| 2 | Avicel PH 102 | 12.75 | 11.47 | 17.21 | 28.69 |
| 3 | Avicel PH105 | 3.36 | 3.02 | 4.53 | 7.56 |
| 4 | Ludiflash | 56.42 | 50.78 | 76.17 | 126.94 |
| 5 | Croscarmellose sodium | 5.00 | 4.50 | 6.75 | 11.25 |
| 6 | Citric acid, anhydrous | 1.25 | 1.13 | 1.69 | 2.81 |
| 7 | Magnesium Stearate | 1.00 | 0.90 | 1.35 | 2.25 |
| | Total | 100.00 | 90.00 | 135.00 | 225.00 |

1* Conversion factor for Epinephrine Bitartrate to Epinephrine is 1.82 : 1.00

FIGURE 6

35mg strength materials/concentrations

| | 35mg Stand-Alone Blend Formulation | | |
|---|---|---|---|
| Item No. | Ingredient | Concentration (%w/w) | mg/Dose |
| 1 | Epinephrine Bitartrate | 28.31 | 63.70 (35)[1] |
| 2 | Avicel PH 102 | 11.33 | 25.49 |
| 3 | Avicel PH105 | 2.99 | 6.72 |
| 4 | Ludiflash | 50.12 | 112.78 |
| 5 | Croscarmellose sodium | 5.00 | 11.25 |
| 6 | Citric acid, anhydrous | 1.25 | 2.81 |
| 7 | Magnesium Stearate | 1.00 | 2.25 |
| | Total | 100.00 | 225.00 |

1* Conversion factor for Epinephrine Bitartrate to Epinephrine is 1.82 : 1.00

SUBLINGUAL EPINEPHRINE TABLETS

CROSS-REFERENCE TO RELATED APPLICATIONS

This application claims priority to of U.S. Provisional Application No. 62/554,979 filed Sep. 6, 2017, the contents of which is incorporated by reference herein in its entirety.

BACKGROUND

Anaphylaxis is a serious allergic reaction, with a rapid onset, and potentially life-threatening. Common causes include insect bites and stings, foods, and medications. Other causes include latex exposure and exercise. Additionally cases may occur without an obvious reason. The mechanism involves the release of mediators from certain types of white blood cells triggered by either immunologic or non-immunologic mechanisms. Diagnosis is based on the presenting symptoms and signs after exposure to a potential allergen. Symptoms include a rapid, weak pulse, skin rash, swelling of the tongue, trouble breathing, nausea, vomiting and a rapid decrease in blood pressure.

Currently, temporary treatment of anaphylaxis is by epinephrine injection ("intramuscular" or "IM") into the thigh muscle of an individual experiencing these symptoms. This allows time to seek further medical intervention, intravenous fluids, and positioning the person flat. Additional doses of epinephrine may be required, and other measures, such as antihistamines and steroids, are complementary. Carrying an epinephrine autoinjector and identification regarding the condition is recommended in people with a history of anaphylaxis.

There is a need for a new method of treating anaphylaxis and a new method of delivering epinephrine to individuals experiencing anaphylaxis because of ineffective delivery and use of the autoinjectors. Many of the traditional alternatives, such as swallowing pills or tablets and inhalers are not applicable because an individual experiencing anaphylaxis may not be able to swallow a pill and airways are constricted. An additional problem with the autoinjectors is effective delivery to the systemic circulation, as injection into the muscle relies upon a small window of opportunity that it will leave the vascular bed and be taken up by the circulation. In an individual experiencing a rapid drop in blood pressure, this may not occur.

SUMMARY OF THE INVENTION

In some embodiments, the invention encompasses a sublingual tablet comprising epinephrine bitartrate and at least one of citric acid, mannitol, avicel, ludiflash, croscarmellose and magnesium stearate. In some embodiments, the sublingual tablet disintegrates in water between about 15 seconds and about 80 seconds.

In some embodiments, the sublingual tablet dissolves in water such that the amount of epinephrine dissolved in water after 120 seconds is between 73.6 and 97.9% of the epinephrine in the tablet. In some embodiments, the sublingual tablet dissolves in water such that the amount of epinephrine dissolved in water after 15 minutes is between 79.3 and 95.9% of the epinephrine in the tablet. In some embodiments, the sublingual tablet dissolves in water such that the amount of epinephrine dissolved in water after 30 minutes is between 83.1 and 97.4% of the epinephrine in the tablet. In some embodiments, the sublingual tablet dissolves in water such that the amount of epinephrine dissolved in water after 45 minutes is between 84.4 and 100% of the epinephrine in the tablet. In some embodiments, the sublingual tablet dissolves in water such that the amount of epinephrine dissolved in water after 60 minutes is between 86.4 and 100% of the epinephrine in the tablet.

In some embodiments, the invention encompasses methods of treating anaphylaxis in a subject comprising administering to the subject a sublingual tablet comprising epinephrine and at least one of citric acid, mannitol, avicel, ludiflash, croscarmellose and magnesium stearate, wherein the subject is experiencing anaphylaxis and has a mean arterial blood pressure of 80 mmHg or less. In some embodiments, the subject is experiencing anaphylaxis and has a mean arterial blood pressure between about 20 mmHg and about 70 mmHg. In some embodiments, the subject is administered rescue medication, such as dexamethasone and/or dopram, in addition to the epinephrine.

In some embodiments, the invention encompasses methods of increasing an amount of epinephrine absorbed by a subject comprising administering a sublingual tablet comprising epinephrine and citric acid, wherein the amount of epinephrine absorbed by the subject is increased compared to the amount of epinephrine absorbed in the absence of citric acid. In some embodiments, the amount of epinephrine absorbed is determined at a predetermined time after administration of the epinephrine. In some embodiments, the predetermined time is 2, 5, 7.5, 10, 20, 30, 40, 50 or 60 minutes after administration of the epinephrine. In some embodiments, the citric acid increases both the amount of epinephrine absorbed and duration of absorption. Without wishing to be bound by any particular theory, the inventors theorize, as described herein, the citric acid aids in creating an epinephrine reservoir in the sublingual mucosa, which affords a longer duration of active absorption.

BRIEF DESCRIPTION OF DRAWINGS

FIG. 1 illustrates dose administration relating to mean arterial pressure drop

FIG. 2 illustrates mean epinephrine plasma pharmacokinetic parameters related to citrate and anaphylaxis.

FIG. 3 illustrates individual pharmacokinetic parameters.

FIG. 4 illustrates an example of a 5 mg strength tablet of the present invention.

FIG. 5 illustrates examples of 10, 15 and 25 mg strength tablets of the present invention.

FIG. 6 illustrates an example of a 35 mg strength tablet of the present invention.

DETAILED DESCRIPTION

Tablets that disintegrate or dissolve rapidly in a subject's mouth without the use of water are convenient for the elderly, young children, patients with swallowing difficulties, and in situations where water is not available. Sublingual administration can produce a faster onset of action than traditional orally administered tablets and the portion absorbed through the sublingual blood vessels bypasses the hepatic first pass metabolic processes.

In other embodiments, the pharmaceutical tablet for buccal or sublingual administration comprising epinephrine can further comprise a pharmaceutically acceptable excipient. In certain embodiments, the pharmaceutically acceptable excipient is selected from the group consisting of: diluents, binders, glidants, lubricants, colorants, flavorants, coating materials, or combinations thereof.

In yet other aspects of the present invention, the disintegrant can be selected from the group consisting of: low-substituted hydroxypropyl celluloses, cross-linked celluloses, cross-linked sodium carboxymethyl celluloses, cross-linked carboxymethyl celluloses, cross-linked croscarmelloses, cross-linked starches, sodium starch glycolate, crospovidone, or combinations thereof.

Conventional tablet processing may be used to manufacture the sublingual epinephrine tablets. The manufactured sublingual epinephrine tablets are fast-disintegrating and have adequate hardness for packaging in bottles and easy handling. In certain embodiments, the manufacturing process involves granulating low-moldable sugars (e.g., mannitol, lactose, glucose, sucrose, and erythritol) that show quick dissolution characteristics with high-moldable sugars (e.g., maltose, sorbitol, trehalose, and maltitol). The epinephrine can be added, along with other standard tableting excipients, during the granulation or blending processes. The tablets are manufactured at a low compression force followed by an optional humidity conditioning treatment to increase tablet hardness. The result is a mixture of excipients that have fast-dissolving and highly moldable characteristics.

In other embodiments, a compressed buccal or sublingual tablet comprising epinephrine is based on a conventional tableting process involving the direct compression of active ingredients, and excipients. The excipients are mixed with the epinephrine and then compressed into tablets. In certain embodiments, epinephrine tablets made with these processes should disintegrate in the mouth in about 15-30 seconds and can be formulated to be bioequivalent, or superior, to intramuscular or subcutaneous injections containing epinephrine.

The correct epinephrine plasma concentrations for the emergency treatment of anaphylaxis are unknown, although the 0.3 mg intramuscular injection is believed to be effective and prevents death from anaphylaxis. In some embodiments, a sublingual tablet containing 35 mg of epinephrine bitartrate produces plasma epinephrine concentrations similar to those achieved by the 0.3 mg epinephrine dose in the thigh as demonstrated using a healthy/non-sedated nor anaphylactic rabbit model. In some embodiments, a sublingual tablet containing 35 mg of epinephrine bitartrate produces plasma epinephrine concentrations superior to those achieved by the 0.3 mg epinephrine dose in the thigh (Epi-Pen) as demonstrated using a sedated and or anaphylactic rabbit model.

While not wishing to be bound to a specific hypothesis, the inventors believe that sublingual epinephrine tablets are superior to intramuscular injections of epinephrine because of the drop in blood pressure associated with anaphylaxis. As blood pressure drops during an episode of anaphylaxis, a subject can become hypotensive, i.e., blood flow is directed away from the extremities to the head and organs in the trunk. In this scenario, intramuscular injection of epinephrine may be insufficient because there is no mechanism that can transport the epinephrine from the site of injection to the systemic blood supply, likely due to decreased and/or inadequate blood pressure. Even without anaphylaxis, subjects with low blood pressure may not absorb epinephrine administered by intramuscular injection. Administration of epinephrine via sublingual tablets of the present invention overcomes this problem. The sublingual tablets of the present invention can be administered to subjects with or without anaphylaxis with low blood pressure.

In some embodiments, the sublingual tablets of the present invention may contain citric acid. While not wishing to be bound to a specific hypothesis, the inventors believe that the citric acid may aid in diffusion of the epinephrine in the epithelial cells of the sublingual mucosa. This facilitation of diffusion may result in increased epinephrine being available for longer, in effect, creating a reservoir of epinephrine that can be beneficial to the subject. Without being bound by any particular theory, the inventors theorize that the citric acid increases the amount of epinephrine absorbed and increases duration of absorption. For example, the citric acid allows rapid initial absorption, while also creating an epinephrine reservoir in the sublingual mucosa. This reservoir creates a longer duration of active absorption. As the circulating levels of epinephrine dissipate, the epinephrine saturating the sublingual mucosa, through diffusion, enters the subject's bloodstream, allowing for longer periods of elevated plasma epinephrine levels.

The following examples are not intended to limit the scope of what the inventors regard as various aspects of the present invention.

Example 1

Production of Epinephrine Sublingual Tablets

Epinephrine sublingual tablets (90 mg tablets) were produced with an effective dose of 35 mg of L-epinephrine. To achieve this dose, 63.7 mg of epinephrine bitartrate were mixed by hand with various excipients in 20 ml of distilled water for batches of 10 tablets. Various blends were made and are depicted below in Table 1

| | Composition (% of total composition) | | | |
|---|---|---|---|---|
| Component | Blend A | Blend B | Blend C | Blend D |
| (−)-Epinephrine(+) bitartrate | 70.7 | 70.7 | 70.7 | 70.7 |
| Mannitol | 15 | 15 | 15 | N/A |
| Avicel PH 102 NF | 3.525 | 6 | 6 | 4 |
| Avicel PH 105 NF | 3.525 | 1.05 | 1.05 | 1.05 |
| Ludiflash | N/A | N/A | N/A | 17 |
| Croscarmellose Sodium NF | 5 | 5 | N/A | 5 |
| Sodium Starch Glycolate | N/A | N/A | 5 | N/A |
| Citric Acid Anhydrous ACS | 1.25 | 1.25 | 1.25 | 1.25 |
| Magnesium Stearate NF, BP, JP | 1 | 1 | 1 | 1 |

Tablets of Blend A were prepared using the following compression forces: 4 kN, 8 kN, 20 kN, 21 kN, 22 kN, 23 kN, 24 kN and 25 kN. Tablets of Blends B-D were prepared using the following compression forces: 2.2 kN and 4 kN. All tablets produced were round, white, shiny and did not crumble.

Example 2

In Vitro Disintegration of Epinephrine Sublingual Tablets

The tablets produced in Example 1 were subjected to a disintegration test. Blend A tablets produced by 20 kN compression force were placed in a vial with 4 ml vial containing 2 ml of water and gently rocked. Disintegration was timed by stopwatch and the tablet was observed to disintegrate after 8 minutes. Blend A tablets produced by 4 kN and 8 kN compression forces were subjected to the same disintegration test. The disintegration time for the 4 kN tablet was 90 seconds and the disintegration time for the 8 kN tablet was 5 minutes.

Blend B-D tablets produced at 4 kN were subjected to the same disintegration test. Disintegration times were as follows: Blend B, 90 seconds; Blend C, 90-120 seconds; and, Blend D, 90-120 seconds.

Blend B-D tablets produced at 2.2 kN were subjected to the same disintegration test. Disintegration times were as follows: Blend B, 30-40 seconds; Blend C, 80 seconds; and, Blend D, 15-30 seconds.

A further two tablets from Blend D were tested and had the following disintegration times: Tablet 1, 36 seconds; Tablet 2, 30 seconds.

Example 3

Manufacture of Epinephrine Tablets

Two lots (Formulation A and Formulation B) of tablets were manufactured. Each batch was 70 tablets and the target size of the tablets was 90 mg. Tablet size was 6 mm in diameter, with a 2 mm thickness. The difference between the two lots was the presence of citric acid. The composition of both lots is presented below in Table 2.

| | Composition (% of total composition) | |
|---|---|---|
| Component | Formulation A | Formulation B |
| (−)-Epinephrine(+) bitartrate | 70.7 | 70.7 |
| Avicel PH 102 NF | 4 | 5.25 |
| Avicel PH 105 NF | 1.05 | 1.05 |
| Ludiflash | 17 | 17 |
| Croscarmellose Sodium NF | 5 | 5 |
| Citric Acid Anhydrous ACS | 1.25 | 0 |
| Magnesium Stearate NF, BP, JP | 1 | 1 |

For Formulation A, the epinephrine bitartrate, Avicel, Ludiflash and ⅔ of the croscarmellose were placed into a 4 oz plastic jar and mixed for 15 minutes using a Turbula blender. The citric acid was ground into a fine powder using a mortar and pestle and was then added to the 4 oz plastic jar with the magnesium stearate and the remaining croscarmellose and mixed for a further 5 mins. Formulation B was made using the same process, with the exclusion of the citric acid.

For each tablet from both formulations, 90 mg of blend was placed into a 6 mm Natoli tablet punch and compressed with a pressure of 500 pounds using a Carver hand press. All tablets from each lot were individually weighed and any tablets below 88 mg or above 92 mg were discarded. Average tablet weight for Formulation A was 90 mg with a % RSD of 1.5 and average tablet weight for Formulation B was 90 mg with a % RSD of 2.0.

Example 4

Dissolution and Analysis

Six tablets from both Formulation A and Formulation B were tested. Following USP dissolution using USP apparatus II (paddles). Dissolution media was water, volume was 500 ml and paddle speed was 50 RPM. Aliquots of 1 ml were taken for analysis at 15, 30, 45 and 60 minutes. Tablets disintegrated within 60 seconds following addition to the dissolution vessels. Material was observed to stay on the bottom of each vessel and slowly lift to float on the surface of the media. Some of the white tablet matter was observed to stick to the paddles. Aliquots were taken into 3 ml plastic syringes and filtered through 0.2 μm PVDF filters into amber HPLC vials for analysis. After 1 hour some tablet material remained on the bottom of the dissolution vessels, some floated and some stuck to the paddles.

Additional dissolution was conducted for a further six tablets from each lot. Tablets were dropped into a 5 ml plastic syringe containing 2 ml of water at 37° C. and allowed to sit for 120 seconds. The syringe plunger was then inserted and the contents of the syringe filtered through a 0.24 μm PVDF filter into an amber HPLC vial. Solutions were further diluted by taking 60 ml and adding water to a final volume of 10 ml for HPLC analysis.

HPLC was performed according to the USP monograph for Epinephrine Injection (USP 39). The method was verified through confirmation of suitability criteria with the column and conditions provided below in Table 3, prior to use for analyzing the tablets (standard area % RSD=0.1, n=6; Rs of between dopamine (RRT 2.0) and epinephrine=13.4).

TABLE 3

| | |
|---|---|
| Column | Agilent Zorbax Eclipse XDB-C8 4.6 × 150 mm, 5 μm, PN 993967-906 |
| Mobile Phase | 50 mM Sodium Phosphate monobasic with 2.4 mM sodium octanesulfonate and 0.13 mM edetate disodium, pH 3.8 mixed 85:15 with methanol |
| Standard concentration | 0.1 mg/ml epinephrine |
| diluent | mobile phase |
| flow rate | 2 ml/min |
| injection volume | 20 ml |
| column temperature | 25° C. |
| detection | 280 nm UV |
| run time | 10 minutes |

Results are set forth in Table 4 below as percentage of epinephrine dissolved.

TABLE 4

| Lot | 15 mins | 30 mins | 45 mins | 60 mins | 120 seconds |
|---|---|---|---|---|---|
| Formulation A | 79.3-95.9 (Ave. 88.1) | 83.1-96.6 (Ave. 89.1) | 84.4-101.2 (Ave. 92.7) | 86.4-101.6 (Ave. 94.1) | 73.6-97.9 (Ave. 86.0) |
| Formulation B | 86.5-95.1 (Ave. 91.0) | 88.0-97.4 (Ave. 92.6) | 90.5-96.4 (Ave. 94.1) | 92.8-95.5 (Ave. 94.0) | 88.7-97.8 (Ave. 92.8) |

Example 5

In Vivo Testing and Pharmacokinectic Analysis of Epinephrine Treatment

Epinephrine sublingual tablets (35 mg Epinephrine, or 35 mg Epinephrine plus 5 mg Citric Acid) and Epinephrine IM injections (1 mg/ml epinephrine hydrochloride) were tested in an animal model as follows.

Using a standard, by weight, randomization procedure, 21 male animals (weighing 3.25 to 3.73 kg at randomization), from a total of 36 male experimentally naïve New Zealand White Hra:(NZW)SPF albino rabbits (approximately 6 to 7 months of age), were assigned to the study as presented in Table 5.

TABLE 5

Main Study Group Assignments

| Group Number | Treatment | Dose (mg/animal) | Dose Volume (mL/rabbit) | Number of Male Animals |
|---|---|---|---|---|
| Induced Anaphylaxis | | | | |
| 1 | Epinephrine Tablet[a] or Injection | 35[b] or 0.30[c] | 0.3[c] | 6 |
| 2 | Epinephrine Tablet[a] | 35 | NA | 6 |
| 3 | Epinephrine Tablet[a] or Injection | 35[b] or 0.30[c] | 0.3[c] | 6 |
| 4 | Saline or Epinephrine Injection | 0 or 0.30[c] | 0.30 | 2 |
| Non-induced Anaphylaxis | | | | |
| 7 | Epinephrine Injection | 0.30 | 0.30 | 3 |

NA - Not applicable
IM - Intramuscular
[a]Tablets with or without citric acid
[b]For tablets (administered via buccal administration)
[c]For injection (administration via IM injection)

Animals assigned to study had body weights within ±20% of the mean body weight. The animals were individually housed in suspended, stainless steel, slatted floor cages. Fluorescent lighting was provided for approximately 12 hours per day. The dark cycle was interrupted intermittently due to study-related activities. Temperature and humidity were maintained to the maximum extent possible within the ranges of 61 to 72° F. and 30 to 70%, respectively.

Lab Diet® (Certified Rabbit Diet #5322, PMI Nutrition International, Inc.) was increased daily during the acclimation period (16 to 29 days) until feeding was approximately 125 g/animal/day. Tap water was available ad libitum via an automatic watering system.

To induce an anaphylactic syndrome, animals in Groups 1 to 4 were administered horse serum (0.2μ sterile filtered) via subcutaneous ("SC") injection at dose volume of 2 mL/animal, followed two days later by an intravenous ("IV") injection at a dose volume of 2 mL/animal.

Forty-one to 44 days following the beginning of the induction period, the animals were sedated by administration of 2 to 3 mg/kg via IM injection of acepromazine, 0.02 mg/kg via IM injection of buprenorphine and sevoflurane via inhalation. Rescue medications of 0.5 mg/kg dexamethasone via IV and 1.1 to 2.8 mg/kg via IV of dopram were administered where needed to five animals. Rescue medications were administered to four animals when the mean arterial pressure ("MAP") dropped below 20 mm Hg. Although the Placebo animal did not fall below 20 mm Hg, rescue medications (minus epinephrine) were administered to confirm that they did not precipitate resolution of anaphylactic conditions.

Following induction of anesthesia, all animals were placed in dorsal recumbency position and an incision was made to locate the right or left femoral artery. An arterial sheath was introduced and advanced into the isolated artery and used to monitor blood pressure. Additionally, an off midline cervical neck incision was made to locate and isolate the left or right external jugular vein for collection of blood and for emergency drug administration, as needed.

In addition, a pulse oximeter was used to monitor the ventilation and oxygen saturation of each animal. Continuous monitoring of blood pressure, heart rate, respiration rate, and oxygen saturation served as a guide to determine as to when to administer epinephrine and to determine if additional rescue treatment was needed.

During the surgery, animal number 702 stopped breathing during placement of the femoral sheath. Attempts to revive the animal failed and no other emergency drugs other than dopram were able to be given as they would have interfered with the study results. The animal was euthanized via an intravenous overdose of sodium pentobarbital followed by an approved method to ensure death.

Following induction of anesthesia and catheter placement, single or repeated challenge doses of 0.5 to 2 mL of filtered horse serum were administered intravenously to each animal in Groups 1 to 4.

Following administration of the challenge dose of horse serum, the test article, epinephrine, was administered once the mean arterial pressure (MAP) dropped below 40 mmHg, dropped by greater than 40% of baseline, or dropped significantly below the baseline MAP. If no change was observed in MAP after 1 minute post-dose of horse serum, a second dose of horse serum was administered. If there was still no change to MAP after 3 minutes post-dose, the study moved forward and epinephrine was given and the animal was deemed a "non-responder". As responders were identified, epinephrine treatments were alternated between citric acid tablets, no citric acid tablets, and injections until all responders were identified and administered the test article.

Prior to tablet administration, the mouth of the animal was wet with 0.5 mL of tap water and the mouth was held shut for 15 to 30 seconds to help dissolve the tablet. For IM administration, the injections were made in the right rear flank of each animal.

Animal number 401 (Group 4) was administered saline, rather than epinephrine, via IM injection into the right rear flank at a dose volume of 0.3 mL.

In the event that MAP dropped significantly (to a value of 20 mmHg or less), rescue medications were administered as described above (with the exception of animal 401, as detailed above). Details of the dose administration are presented in FIG. 1.

Plasma samples were collected in potassium EDTA anticoagulant vials and assayed for epinephrine content by a LC-MS/MS method. Epinephrine-$d_6$ was used as the standard. Each 50 μL aliquot of standard, QC sample, and study sample was mixed with 200 μL of working internal standard solution (25 ng/mL in acetonitrile/methanol (50/50, v/v)). The sample was centrifuged, and a 200 μL aliquot of the resulting supernatant was transferred to a clean 96-well plate. The sample was evaporated and reconstituted with 100 mL of water/formic acid (100/0.1, v/v). An aliquot was injected onto an LC-MS/MS system for analysis.

The liquid chromatography system used an ACE 5 C18 column, 50×2.1 mm (5 μm particle size) with an isocratic flow consisting of water/formic acid (100/0.1, v/v) and methanol/formic acid (100/0.05, v/v) at a flow rate of 400 μL/minute. The analyte and internal standard were detected using an SCIEX API 5000 triple quadrupole LC-MS/MS system equipped with an ESI (TurboIonSpray®) ionization source operated in the positive ion mode.

The following MRM transitions of the respective [M+H]+ ions were used to monitor epinephrine and epinephrine-$d_6$. Epinephrine: transition monitored: m/z 184 to 166; retention time: 0.4-0.6 minutes. Epinephrine-$d_6$: transition monitored:

m/z 190 to 172; retention time: 0.4-0.6 minutes. The lower limit of quantitation was 1 ng/ml and a linear 1/x2 weighting regression analysis was used. Results from the plasma samples are presented in Table 6.

TABLE 6

| Subject Group | Analyte | Dose | Dose Units | Subject | Gender | Day Nominal | Hour Nominal | Concentration (ng/mL) | LLQ |
|---|---|---|---|---|---|---|---|---|---|
| 1 | Epinephrine | 35 | mg | 101 | Male | 1 | 0 | 2.85 | 1 ng/mL |
| 1 | Epinephrine | 35 | mg | 101 | Male | 1 | 0.033 | 5.69 | 1 ng/mL |
| 1 | Epinephrine | 35 | mg | 101 | Male | 1 | 0.083 | 3.38 | 1 ng/mL |
| 1 | Epinephrine | 35 | mg | 101 | Male | 1 | 0.125 | 3.17 | 1 ng/mL |
| 1 | Epinephrine | 35 | mg | 101 | Male | 1 | 0.167 | 5.94 | 1 ng/mL |
| 1 | Epinephrine | 35 | mg | 101 | Male | 1 | 0.25 | 3.68 | 1 ng/mL |
| 1 | Epinephrine | 35 | mg | 101 | Male | 1 | 0.333 | 11.1 | 1 ng/mL |
| 1 | Epinephrine | 35 | mg | 101 | Male | 1 | 0.5 | 27.0 | 1 ng/mL |
| 1 | Epinephrine | 35 | mg | 101 | Male | 1 | 0.75 | 13.0 | 1 ng/mL |
| 1 | Epinephrine | 35 | mg | 101 | Male | 1 | 1 | 13.8 | 1 ng/mL |
| 2 | Epinephrine | 35 | mg | 102 | Male | 1 | 0 | 2.19 | 1 ng/mL |
| 2 | Epinephrine | 35 | mg | 102 | Male | 1 | 0.033 | 7.22 | 1 ng/mL |
| 2 | Epinephrine | 35 | mg | 102 | Male | 1 | 0.083 | 4.37 | 1 ng/mL |
| 2 | Epinephrine | 35 | mg | 102 | Male | 1 | 0.125 | 7.08 | 1 ng/mL |
| 2 | Epinephrine | 35 | mg | 102 | Male | 1 | 0.167 | 6.64 | 1 ng/mL |
| 2 | Epinephrine | 35 | mg | 102 | Male | 1 | 0.25 | 14.9 | 1 ng/mL |
| 2 | Epinephrine | 35 | mg | 102 | Male | 1 | 0.333 | 8.61 | 1 ng/mL |
| 2 | Epinephrine | 35 | mg | 102 | Male | 1 | 0.5 | 17.3 | 1 ng/mL |
| 2 | Epinephrine | 35 | mg | 102 | Male | 1 | 0.75 | 19.7 | 1 ng/mL |
| 2 | Epinephrine | 35 | mg | 102 | Male | 1 | 1 | 61.2 | 1 ng/mL |
| 3 | Epinephrine | 0.3 | mg | 103 | Male | 1 | 0 | BLQ | 1 ng/mL |
| 3 | Epinephrine | 0.3 | mg | 103 | Male | 1 | 0.033 | 1.62 | 1 ng/mL |
| 3 | Epinephrine | 0.3 | mg | 103 | Male | 1 | 0.083 | 2.45 | 1 ng/mL |
| 3 | Epinephrine | 0.3 | mg | 103 | Male | 1 | 0.125 | 1.57 | 1 ng/mL |
| 3 | Epinephrine | 0.3 | mg | 103 | Male | 1 | 0.167 | 2.40 | 1 ng/mL |
| 3 | Epinephrine | 0.3 | mg | 103 | Male | 1 | 0.25 | 1.56 | 1 ng/mL |
| 3 | Epinephrine | 0.3 | mg | 103 | Male | 1 | 0.333 | 1.97 | 1 ng/mL |
| 3 | Epinephrine | 0.3 | mg | 103 | Male | 1 | 0.5 | 2.39 | 1 ng/mL |
| 3 | Epinephrine | 0.3 | mg | 103 | Male | 1 | 0.75 | 3.31 | 1 ng/mL |
| 3 | Epinephrine | 0.3 | mg | 103 | Male | 1 | 1 | 5.00 | 1 ng/mL |
| 3 | Epinephrine | 0.3 | mg | 104 | Male | 1 | 0 | 2.29 | 1 ng/mL |
| 3 | Epinephrine | 0.3 | mg | 104 | Male | 1 | 0.033 | 3.80 | 1 ng/mL |
| 3 | Epinephrine | 0.3 | mg | 104 | Male | 1 | 0.083 | 2.30 | 1 ng/mL |
| 3 | Epinephrine | 0.3 | mg | 104 | Male | 1 | 0.125 | 4.43 | 1 ng/mL |
| 3 | Epinephrine | 0.3 | mg | 104 | Male | 1 | 0.167 | 5.36 | 1 ng/mL |
| 3 | Epinephrine | 0.3 | mg | 104 | Male | 1 | 0.25 | 6.73 | 1 ng/mL |
| 3 | Epinephrine | 0.3 | mg | 104 | Male | 1 | 0.333 | 10.5 | 1 ng/mL |
| 3 | Epinephrine | 0.3 | mg | 104 | Male | 1 | 0.5 | 8.28 | 1 ng/mL |
| 3 | Epinephrine | 0.3 | mg | 104 | Male | 1 | 0.75 | 8.51 | 1 ng/mL |
| 3 | Epinephrine | 0.3 | mg | 104 | Male | 1 | 1 | 14.0 | 1 ng/mL |
| 1 | Epinephrine | 35 | mg | 105 | Male | 1 | 0 | 1.38 | 1 ng/mL |
| 1 | Epinephrine | 35 | mg | 105 | Male | 1 | 0.033 | 2.03 | 1 ng/mL |
| 1 | Epinephrine | 35 | mg | 105 | Male | 1 | 0.083 | 2.00 | 1 ng/mL |
| 1 | Epinephrine | 35 | mg | 105 | Male | 1 | 0.125 | 11.3 | 1 ng/mL |
| 1 | Epinephrine | 35 | mg | 105 | Male | 1 | 0.167 | 20.5 | 1 ng/mL |
| 1 | Epinephrine | 35 | mg | 105 | Male | 1 | 0.25 | 36.2 | 1 ng/mL |
| 1 | Epinephrine | 35 | mg | 105 | Male | 1 | 0.333 | 45.6 | 1 ng/mL |
| 1 | Epinephrine | 35 | mg | 105 | Male | 1 | 0.5 | 57.3 | 1 ng/mL |
| 1 | Epinephrine | 35 | mg | 105 | Male | 1 | 0.75 | 50.9 | 1 ng/mL |
| 1 | Epinephrine | 35 | mg | 105 | Male | 1 | 1 | 60.7 | 1 ng/mL |
| 1 | Epinephrine | 35 | mg | 106 | Male | 1 | 0 | 6.60 | 1 ng/mL |
| 1 | Epinephrine | 35 | mg | 106 | Male | 1 | 0.033 | 108 | 1 ng/mL |
| 1 | Epinephrine | 35 | mg | 106 | Male | 1 | 0.083 | 13.1 | 1 ng/mL |
| 1 | Epinephrine | 35 | mg | 106 | Male | 1 | 0.125 | 3.07 | 1 ng/mL |
| 1 | Epinephrine | 35 | mg | 106 | Male | 1 | 0.167 | 5.47 | 1 ng/mL |
| 1 | Epinephrine | 35 | mg | 106 | Male | 1 | 0.25 | 3.56 | 1 ng/mL |
| 1 | Epinephrine | 35 | mg | 106 | Male | 1 | 0.333 | 4.00 | 1 ng/mL |
| 1 | Epinephrine | 35 | mg | 106 | Male | 1 | 0.5 | 8.87 | 1 ng/mL |
| 1 | Epinephrine | 35 | mg | 106 | Male | 1 | 0.75 | 14.8 | 1 ng/mL |
| 1 | Epinephrine | 35 | mg | 106 | Male | 1 | 1 | 84.9 | 1 ng/mL |
| 1 | Epinephrine | 35 | mg | 201 | Male | 1 | 0 | 2.00 | 2 ng/mL |
| 1 | Epinephrine | 35 | mg | 201 | Male | 1 | 0.033 | 10.5 | 2 ng/mL |
| 1 | Epinephrine | 35 | mg | 201 | Male | 1 | 0.083 | 3.72 | 2 ng/mL |
| 1 | Epinephrine | 35 | mg | 201 | Male | 1 | 0.125 | 3.40 | 2 ng/mL |
| 1 | Epinephrine | 35 | mg | 201 | Male | 1 | 0.167 | 7.53 | 2 ng/mL |
| 1 | Epinephrine | 35 | mg | 201 | Male | 1 | 0.25 | 5.33 | 2 ng/mL |
| 1 | Epinephrine | 35 | mg | 201 | Male | 1 | 0.333 | 5.94 | 2 ng/mL |
| 1 | Epinephrine | 35 | mg | 201 | Male | 1 | 0.5 | 5.72 | 2 ng/mL |
| 1 | Epinephrine | 35 | mg | 201 | Male | 1 | 0.75 | 8.17 | 2 ng/mL |
| 1 | Epinephrine | 35 | mg | 201 | Male | 1 | 1 | 10.2 | 2 ng/mL |
| 2 | Epinephrine | 35 | mg | 202 | Male | 1 | 0 | 2.61 | 2 ng/mL |
| 2 | Epinephrine | 35 | mg | 202 | Male | 1 | 0.033 | 40.1 | 2 ng/mL |

TABLE 6-continued

| Subject Group | Analyte | Dose | Dose Units | Subject | Gender | Day Nominal | Hour Nominal | Concentration (ng/mL) | LLQ |
|---|---|---|---|---|---|---|---|---|---|
| 2 | Epinephrine | 35 | mg | 202 | Male | 1 | 0.083 | 12.7 | 2 ng/mL |
| 2 | Epinephrine | 35 | mg | 202 | Male | 1 | 0.125 | 39.5 | 2 ng/mL |
| 2 | Epinephrine | 35 | mg | 202 | Male | 1 | 0.167 | 28.2 | 2 ng/mL |
| 2 | Epinephrine | 35 | mg | 202 | Male | 1 | 0.25 | 52.5 | 2 ng/mL |
| 2 | Epinephrine | 35 | mg | 202 | Male | 1 | 0.333 | 37.9 | 2 ng/mL |
| 2 | Epinephrine | 35 | mg | 202 | Male | 1 | 0.5 | 24.2 | 2 ng/mL |
| 2 | Epinephrine | 35 | mg | 202 | Male | 1 | 0.75 | 21.6 | 2 ng/mL |
| 2 | Epinephrine | 35 | mg | 202 | Male | 1 | 1 | 26.4 | 2 ng/mL |
| 1 | Epinephrine | 35 | mg | 203 | Male | 1 | 0 | 2.80 | 2 ng/mL |
| 1 | Epinephrine | 35 | mg | 203 | Male | 1 | 0.033 | 5.66 | 2 ng/mL |
| 1 | Epinephrine | 35 | mg | 203 | Male | 1 | 0.083 | 5.64 | 2 ng/mL |
| 1 | Epinephrine | 35 | mg | 203 | Male | 1 | 0.125 | 11.8 | 2 ng/mL |
| 1 | Epinephrine | 35 | mg | 203 | Male | 1 | 0.167 | 16.8 | 2 ng/mL |
| 1 | Epinephrine | 35 | mg | 203 | Male | 1 | 0.25 | 14.4 | 2 ng/mL |
| 1 | Epinephrine | 35 | mg | 203 | Male | 1 | 0.333 | 53.3 | 2 ng/mL |
| 1 | Epinephrine | 35 | mg | 203 | Male | 1 | 0.5 | 18.0 | 2 ng/mL |
| 1 | Epinephrine | 35 | mg | 203 | Male | 1 | 0.75 | 25.6 | 2 ng/mL |
| 1 | Epinephrine | 35 | mg | 203 | Male | 1 | 1 | 13.3 | 2 ng/mL |
| 2 | Epinephrine | 35 | mg | 205 | Male | 1 | 0 | 1.06 | 1 ng/mL |
| 2 | Epinephrine | 35 | mg | 205 | Male | 1 | 0.033 | 28.9 | 1 ng/mL |
| 2 | Epinephrine | 35 | mg | 205 | Male | 1 | 0.083 | 4.00 | 1 ng/mL |
| 2 | Epinephrine | 35 | mg | 205 | Male | 1 | 0.125 | 2.59 | 1 ng/mL |
| 2 | Epinephrine | 35 | mg | 205 | Male | 1 | 0.167 | 2.12 | 1 ng/mL |
| 2 | Epinephrine | 35 | mg | 205 | Male | 1 | 0.25 | 1.60 | 1 ng/mL |
| 2 | Epinephrine | 35 | mg | 205 | Male | 1 | 0.333 | 1.47 | 1 ng/mL |
| 2 | Epinephrine | 35 | mg | 205 | Male | 1 | 0.5 | 1.95 | 1 ng/mL |
| 2 | Epinephrine | 35 | mg | 205 | Male | 1 | 0.75 | 2.07 | 1 ng/mL |
| 2 | Epinephrine | 35 | mg | 205 | Male | 1 | 1 | 3.01 | 1 ng/mL |
| 2 | Epinephrine | 35 | mg | 206 | Male | 1 | 0 | 2.03 | 2 ng/mL |
| 2 | Epinephrine | 35 | mg | 206 | Male | 1 | 0.033 | 8.96 | 2 ng/mL |
| 2 | Epinephrine | 35 | mg | 206 | Male | 1 | 0.083 | 4.92 | 2 ng/mL |
| 2 | Epinephrine | 35 | mg | 206 | Male | 1 | 0.125 | 3.76 | 2 ng/mL |
| 2 | Epinephrine | 35 | mg | 206 | Male | 1 | 0.167 | 3.65 | 2 ng/mL |
| 2 | Epinephrine | 35 | mg | 206 | Male | 1 | 0.25 | 7.38 | 2 ng/mL |
| 2 | Epinephrine | 35 | mg | 206 | Male | 1 | 0.333 | 3.38 | 2 ng/mL |
| 2 | Epinephrine | 35 | mg | 206 | Male | 1 | 0.5 | 4.53 | 2 ng/mL |
| 2 | Epinephrine | 35 | mg | 206 | Male | 1 | 0.75 | 7.57 | 2 ng/mL |
| 2 | Epinephrine | 35 | mg | 206 | Male | 1 | 1 | 8.05 | 2 ng/mL |
| 1 | Epinephrine | 35 | mg | 301 | Male | 1 | 0 | 1.49 | 1 ng/mL |
| 1 | Epinephrine | 35 | mg | 301 | Male | 1 | 0.033 | 4.88 | 2 ng/mL |
| 1 | Epinephrine | 35 | mg | 301 | Male | 1 | 0.083 | 7.61 | 2 ng/mL |
| 1 | Epinephrine | 35 | mg | 301 | Male | 1 | 0.125 | 6.79 | 2 ng/mL |
| 1 | Epinephrine | 35 | mg | 301 | Male | 1 | 0.167 | 11.4 | 2 ng/mL |
| 1 | Epinephrine | 35 | mg | 301 | Male | 1 | 0.25 | 15.9 | 2 ng/mL |
| 1 | Epinephrine | 35 | mg | 301 | Male | 1 | 0.333 | 10.3 | 2 ng/mL |
| 1 | Epinephrine | 35 | mg | 301 | Male | 1 | 0.5 | 2.60 | 2 ng/mL |
| 1 | Epinephrine | 35 | mg | 301 | Male | 1 | 0.75 | 3.19 | 2 ng/mL |
| 1 | Epinephrine | 35 | mg | 301 | Male | 1 | 1 | 2.08 | 2 ng/mL |
| 2 | Epinephrine | 35 | mg | 302 | Male | 1 | 0 | 5.66 | 2 ng/mL |
| 2 | Epinephrine | 35 | mg | 302 | Male | 1 | 0.033 | 13.5 | 2 ng/mL |
| 2 | Epinephrine | 35 | mg | 302 | Male | 1 | 0.083 | 7.23 | 2 ng/mL |
| 2 | Epinephrine | 35 | mg | 302 | Male | 1 | 0.125 | 8.49 | 2 ng/mL |
| 2 | Epinephrine | 35 | mg | 302 | Male | 1 | 0.167 | 7.75 | 2 ng/mL |
| 2 | Epinephrine | 35 | mg | 302 | Male | 1 | 0.25 | 4.82 | 2 ng/mL |
| 2 | Epinephrine | 35 | mg | 302 | Male | 1 | 0.333 | 7.14 | 2 ng/mL |
| 2 | Epinephrine | 35 | mg | 302 | Male | 1 | 0.5 | 4.76 | 2 ng/mL |
| 2 | Epinephrine | 35 | mg | 302 | Male | 1 | 0.75 | 5.41 | 2 ng/mL |
| 2 | Epinephrine | 35 | mg | 302 | Male | 1 | 1 | 6.75 | 2 ng/mL |
| 3 | Epinephrine | 0.3 | mg | 303 | Male | 1 | 0 | BLQ | 1 ng/mL |
| 3 | Epinephrine | 0.3 | mg | 303 | Male | 1 | 0.033 | 5.38 | 2 ng/mL |
| 3 | Epinephrine | 0.3 | mg | 303 | Male | 1 | 0.083 | 6.43 | 2 ng/mL |
| 3 | Epinephrine | 0.3 | mg | 303 | Male | 1 | 0.125 | 4.79 | 2 ng/mL |
| 3 | Epinephrine | 0.3 | mg | 303 | Male | 1 | 0.167 | 4.97 | 2 ng/mL |
| 3 | Epinephrine | 0.3 | mg | 303 | Male | 1 | 0.25 | 4.49 | 2 ng/mL |
| 3 | Epinephrine | 0.3 | mg | 303 | Male | 1 | 0.333 | 6.29 | 2 ng/mL |
| 3 | Epinephrine | 0.3 | mg | 303 | Male | 1 | 0.5 | 4.42 | 2 ng/mL |
| 3 | Epinephrine | 0.3 | mg | 303 | Male | 1 | 0.75 | 5.47 | 2 ng/mL |
| 3 | Epinephrine | 0.3 | mg | 303 | Male | 1 | 1 | 3.09 | 1 ng/mL |
| 1 | Epinephrine | 35 | mg | 304 | Male | 1 | 0 | 4.24 | 2 ng/mL |
| 1 | Epinephrine | 35 | mg | 304 | Male | 1 | 0.033 | 12.7 | 2 ng/mL |
| 1 | Epinephrine | 35 | mg | 304 | Male | 1 | 0.083 | 8.70 | 2 ng/mL |
| 1 | Epinephrine | 35 | mg | 304 | Male | 1 | 0.125 | 30.3 | 2 ng/mL |
| 1 | Epinephrine | 35 | mg | 304 | Male | 1 | 0.167 | 40.9 | 2 ng/mL |
| 1 | Epinephrine | 35 | mg | 304 | Male | 1 | 0.25 | 4.99 | 2 ng/mL |
| 1 | Epinephrine | 35 | mg | 304 | Male | 1 | 0.333 | 2.60 | 2 ng/mL |
| 1 | Epinephrine | 35 | mg | 304 | Male | 1 | 0.5 | 5.33 | 2 ng/mL |
| 1 | Epinephrine | 35 | mg | 304 | Male | 1 | 0.75 | 6.16 | 2 ng/mL |

TABLE 6-continued

| Subject Group | Analyte | Dose | Dose Units | Subject | Gender | Day Nominal | Hour Nominal | Concentration (ng/mL) | LLQ |
|---|---|---|---|---|---|---|---|---|---|
| 1 | Epinephrine | 35 | mg | 304 | Male | 1 | 1 | 9.02 | 2 ng/mL |
| 2 | Epinephrine | 35 | mg | 305 | Male | 1 | 0 | 3.68 | 2 ng/mL |
| 2 | Epinephrine | 35 | mg | 305 | Male | 1 | 0.033 | 23.9 | 2 ng/mL |
| 2 | Epinephrine | 35 | mg | 305 | Male | 1 | 0.083 | 56.0 | 2 ng/mL |
| 2 | Epinephrine | 35 | mg | 305 | Male | 1 | 0.125 | 31.6 | 2 ng/mL |
| 2 | Epinephrine | 35 | mg | 305 | Male | 1 | 0.167 | 25.7 | 2 ng/mL |
| 2 | Epinephrine | 35 | mg | 306 | Male | 1 | 0 | 7.59 | 2 ng/mL |
| 2 | Epinephrine | 35 | mg | 306 | Male | 1 | 0.033 | 10.2 | 2 ng/mL |
| 2 | Epinephrine | 35 | mg | 306 | Male | 1 | 0.083 | 9.28 | 2 ng/mL |
| 2 | Epinephrine | 35 | mg | 306 | Male | 1 | 0.125 | 38.7 | 2 ng/mL |
| 2 | Epinephrine | 35 | mg | 306 | Male | 1 | 0.167 | 6.53 | 2 ng/mL |
| 2 | Epinephrine | 35 | mg | 306 | Male | 1 | 0.25 | 7.70 | 2 ng/mL |
| 2 | Epinephrine | 35 | mg | 306 | Male | 1 | 0.333 | 5.20 | 2 ng/mL |
| 2 | Epinephrine | 35 | mg | 306 | Male | 1 | 0.5 | 6.94 | 2 ng/mL |
| 2 | Epinephrine | 35 | mg | 306 | Male | 1 | 0.75 | 6.20 | 2 ng/mL |
| 2 | Epinephrine | 35 | mg | 306 | Male | 1 | 1 | 10.6 | 2 ng/mL |
| 4 | Epinephrine | 0 | mg | 401 | Male | 1 | 0 | 2.02 | 1 ng/mL |
| 4 | Epinephrine | 0 | mg | 401 | Male | 1 | 0.033 | 4.06 | 2 ng/mL |
| 4 | Epinephrine | 0 | mg | 401 | Male | 1 | 0.083 | 5.31 | 2 ng/mL |
| 4 | Epinephrine | 0 | mg | 401 | Male | 1 | 0.125 | 5.72 | 2 ng/mL |
| 4 | Epinephrine | 0 | mg | 401 | Male | 1 | 0.167 | 6.96 | 2 ng/mL |
| 4 | Epinephrine | 0 | mg | 401 | Male | 1 | 0.25 | 1.47 | 1 ng/mL |
| 4 | Epinephrine | 0 | mg | 401 | Male | 1 | 0.333 | 5.54 | 2 ng/mL |
| 4 | Epinephrine | 0 | mg | 401 | Male | 1 | 0.5 | 6.35 | 2 ng/mL |
| 4 | Epinephrine | 0 | mg | 401 | Male | 1 | 0.75 | 2.38 | 2 ng/mL |
| 4 | Epinephrine | 0 | mg | 401 | Male | 1 | 1 | 1.91 | 1 ng/mL |
| 7 | Epinephrine | 0.3 | mg | 701 | Male | 1 | 0 | 2.48 | 2 ng/mL |
| 7 | Epinephrine | 0.3 | mg | 701 | Male | 1 | 0.033 | 2.75 | 1 ng/mL |
| 7 | Epinephrine | 0.3 | mg | 701 | Male | 1 | 0.083 | 4.32 | 2 ng/mL |
| 7 | Epinephrine | 0.3 | mg | 701 | Male | 1 | 0.125 | 5.73 | 2 ng/mL |
| 7 | Epinephrine | 0.3 | mg | 701 | Male | 1 | 0.167 | 4.76 | 2 ng/mL |
| 7 | Epinephrine | 0.3 | mg | 701 | Male | 1 | 0.25 | 2.44 | 2 ng/mL |
| 7 | Epinephrine | 0.3 | mg | 701 | Male | 1 | 0.333 | BLQ | 2 ng/mL |
| 7 | Epinephrine | 0.3 | mg | 701 | Male | 1 | 0.5 | 2.06 | 2 ng/mL |
| 7 | Epinephrine | 0.3 | mg | 701 | Male | 1 | 0.75 | 2.84 | 2 ng/mL |
| 7 | Epinephrine | 0.3 | mg | 701 | Male | 1 | 1 | 3.10 | 2 ng/mL |
| 7 | Epinephrine | 0.3 | mg | 703 | Male | 1 | 0 | 1.92 | 1 ng/mL |
| 7 | Epinephrine | 0.3 | mg | 703 | Male | 1 | 0.033 | 8.06 | 1 ng/mL |
| 7 | Epinephrine | 0.3 | mg | 703 | Male | 1 | 0.083 | 6.60 | 1 ng/mL |
| 7 | Epinephrine | 0.3 | mg | 703 | Male | 1 | 0.125 | 3.53 | 1 ng/mL |
| 7 | Epinephrine | 0.3 | mg | 703 | Male | 1 | 0.167 | 2.32 | 1 ng/mL |
| 7 | Epinephrine | 0.3 | mg | 703 | Male | 1 | 0.25 | 3.50 | 1 ng/mL |
| 7 | Epinephrine | 0.3 | mg | 703 | Male | 1 | 0.333 | 3.78 | 1 ng/mL |
| 7 | Epinephrine | 0.3 | mg | 703 | Male | 1 | 0.5 | 2.86 | 1 ng/mL |
| 7 | Epinephrine | 0.3 | mg | 703 | Male | 1 | 0.75 | 5.36 | 1 ng/mL |
| 7 | Epinephrine | 0.3 | mg | 703 | Male | 1 | 1 | 5.17 | 1 ng/mL |

Plasma concentration-time profiles from placebo and epinephrine-treated animals were analyzed. Concentrations less than the lower limit of quantitation (LLOQ, <1.00 ng/mL) were reported as and set to zero. For each animal, the following pharmacokinetic parameters were determined: maximum observed plasma concentration ($C_{max}$), time of maximum observed plasma concentration ($T_{max}$), and area under the plasma concentration-time curve (AUC). The AUC from time 0 to 1 hour ($AUC_{0-60\ min}$) and the AUC from time 0 to the time of the final quantifiable sample ($AUCT_{last}$) were calculated by the linear trapezoidal method for all animals with at least three consecutive quantifiable concentrations.

The formulation ratio was calculated using the following formula: Formulation Ratio=Mean $AUC_{0-60\ min\ Buccal\ Citrate}$ ÷ Mean $AUC_{0-60\ min\ Buccal\ No\ citrate}$. The Induced Anaphylaxis to Non-induced anaphylaxis ratio was calculated using the following formula: Induced Anaphylaxis:Non-Induced Anaphylaxis=Mean $AUC_{0-60\ min\ Induced\ Anaphylaxis\ IM}$ ÷ Mean $AUC_{0-60\ min\ Non-induced\ Anaphylaxis\ IM}$. Relative bioavailability (expressed as a percent) was calculated using the following formula: Relative Bioavailability=[$AUC_{0-60\ min}$/$Dose_{Buccal\ (citrate\ and/or\ no\ citrate)}$] ÷ [$AUC_{0-60\ min}$/$Dose_{Intramuscular\ (induced\ and/or\ non-induced)}$]*100.

Mean epinephrine plasma pharmacokinetic parameters for citrate or no citrate combined and induced and non-induced anaphylaxis combined are provided in FIG. 2. Individual pharmacokinetic parameters are provided in FIG. 3.

Dissolution and Disintegration Rates

In some embodiments, the time for full disintegration is preferred to be from 120 to 101 seconds; from 100 to 90 seconds; and from 90 to 80 seconds. In some embodiments, full disintegration is preferred to occur in less than 100 seconds. Depending on materials used in the manufacture and the manufacturing process, the disintegration rates may average from 50 seconds to about 200 seconds; from 50 seconds to about 120 seconds; from 50 seconds to about 100 seconds; and less than 100 seconds.

In some embodiments, it is preferred that there is from 12% to 100% dissolution within 5 minutes; from 35% to 100% dissolution within 5 minutes; from 50% to 100% dissolution within 5 minutes; and from 75% to 100% dissolution within 5 minutes. In some embodiments, it is preferred that there is from 45% to 100% dissolution within 10 minutes; from 50% to 100% dissolution within 10 minutes; and from 90% to 100% dissolution within 10 minutes. In some embodiments, it is preferred that there is from 95% to 100% dissolution within 15 minutes to 30 minutes. It will be understood that variations in dissolution times may occur based on manufacturing methodology.

The dissolution and disintegration rates are for the dose forms provided for herein. As will be appreciated, dose amounts of epinephrine may be in the amounts of 5 mg to 35 mg. In some embodiments, epinephrine may be present in amounts between 5 mg and 35 mg. For example, doses within the scope of this disclosure would include 5 mg, 10 mg, 15 mg, 25 mg, 30 mg, and 35 mg, as well as those amounts provided within the ranges herein.

A 5 mg strength tablet of active ingredient epinephrine is provided in FIG. 4, for example.

Tablet formulations of 10 mg, 15 mg and 25 mg of the active ingredient epinephrine are also provided as seen in FIG. 5, for example.

Tablets of 35 mg of active ingredient of epinephrine per dose are also provided, as seen in FIG. 6, for example.

It will be appreciated that certain other ingredients may be added, substituted or combined in the formulation without departing from the disclosure of the invention.

Prophylaxis for Immunotherapy

Immunotherapy is a prolonged and expensive treatment; however, it is the only thing having the potential to alter the course of allergies. One of the biggest concerns with immunotherapy is its potential to cause severe or even fatal systemic reactions. Using the present invention concomitantly with allergen injections can not only possibly waylay that fear, but may allow a higher allergen concentration of exposure to potentially shorten the course of immunotherapy and provide protection sooner. Because allergen immunotherapy introduces an allergen into an allergic individual, hypersensitivity reactions are probably unavoidable. There are, however, potential measures to minimize the risk and effective therapy to treat any such reactions.

Due to its fast onset of action, it may be suggested that the patient receiving immunotherapy place a tablet of t sublingually at the first sign of any adverse event resulting from an immunotherapy injection of pre-determined allergen. This could block the cascade into anaphylaxis before it begins and potentially mitigate biphasic anaphylaxis due to its longer-acting capabilities.

Concomitant Use During Cardio-Pulmonary Resuscitation

Epinephrine is the primary drug administered during cardiopulmonary resuscitation (CPR) to reverse cardiac arrest. Epinephrine increases arterial blood pressure and coronary perfusion during CPR via alpha-1-adrenoceptor agonist effects that serve to increase myocardial and cerebral blood flow. Clinical data suggests that epinephrine increases a short-term return of pulse during life-threatening cardiac event. There is no data presently showing increase in long term benefit; however, because the present invention gives significant blood concentrations even during hypotension where intramuscular administration potentially does not, means that dosing studies need to be carried out for long term data. Once spontaneous circulation is restored, alpha- and/or beta-adrenergic agonists may be needed for circulatory support once hospitalized/stable.

Because the current epinephrine-containing therapy is invasive and specialized to administer, as well as expensive to acquire, store and replace, it is not a current consideration for CPR by the average bystander or small business. It is; however, protocol in the clinical setting during Advanced Cardiac Life Support (ACLS). Due to the present invention's (methods and compositions) cost, ease of administration and storage stability, it lends itself to be provided in AED appliances on site.

Once it is determined that CPR may be administered, prior to chest compressions, one dose of a composition of the present invention can be immediately placed under the tongue before proceeding with chest compressions. The compositions of the present invention enter the blood stream within 2 minutes, suggesting that pulse can return rather quickly which could be helpful to the one administering CPR, particularly if the person is performing compressions alone and may fatigue before the patient stabilizes. The person would maintain the procedure until pulse returns and EMT arrives to be informed that a single dose was administered prior to chest compressions.

Single Use for Hypoglycemia in Diabetics

Fear of a severe hypoglycemic reaction is a major obstacle to achieving near-normal plasma glucose levels. Although parenteral glucagon is effective in treating these reactions, it is cumbersome to use, causes severe nausea, and is impractical in the home or school setting. Alternatively, the sublingual use of compositions of the present invention may be used by all care providers be it clinical or non-clinical, e.g., a family member. Using compositions of the present invention to treat hypoglycemia may be an effective, safe, and easy-to-use alternative to glucagon, particularly in children. Though a much smaller intramuscular dose of the active has been shown to be minimally effective, the herein described compositions' higher blood concentration and faster acting formulation, with prolonged activity serves to provide a viable alternative in the non-clinical setting.

A composition of the present invention is a single step, stable formulation, without the cost, special training or practice needed for administration as present therapies. Hypoglycemia (low blood sugar) is a condition characterized by abnormally low blood glucose (sugar) levels—usually less than 70 mg/dL. A composition of the present invention is administered in a single dose at the onset of hypoglycemia or early symptoms, including: sweating; dizziness; palpitation; tremors; hunger; restlessness; tingling in the hands, feet, lips or tongue; lightheadedness; inability to concentrate; headache; drowsiness; sleep disturbances; anxiety; blurred vision; slurred speech; depressed mood; abnormal behavior; unsteady movement; personality changes; and combinations thereof. If not treated, the symptoms may progress to severe hypoglycemia, with disorientation, unconsciousness, seizures, and potentially death.

What is claimed is:

1. A sublingual epinephrine tablet comprising:
    an effective amount of epinephrine bitartrate and citric acid for increasing and maintaining a blood plasma level of epinephrine in a subject above a pre-dose level of epinephrine for more than 30 minutes, and
    pharmaceutically acceptable excipients,
        wherein the citric acid, in the effective amount of epinephrine bitartrate and citric acid, is not an excipient wherein the epinephrine bitartrate is in an amount between 5 mg and 35 mg and wherein the citric acid is in an amount between 2.81 mg and 5 mg.

2. The sublingual epinephrine tablet of claim 1, wherein the epinephrine bitartrate is in an amount selected from 5 mg, 10 mg, 15 mg, 25 mg and 35 mg.

3. A sublingual epinephrine tablet comprising:
    an effective amount of epinephrine bitartrate and citric acid for increasing and maintaining a blood plasma level of epinephrine in a subject above a pre-dose level of epinephrine for more than 30 minutes, and pharmaceutically acceptable excipients, wherein the epinephrine bitartrate is in an amount of 35 mg and the citric acid is in an amount of 5 mg, and wherein the citric acid, in the effective amount of epinephrine bitartrate and citric acid, is not an excipient.

4. A sublingual epinephrine tablet comprising:

an effective amount of epinephrine bitartrate and citric acid for increasing and maintaining a blood plasma level of epinephrine in a subject above a pre-dose level of epinephrine for more than 30 minutes, and pharmaceutically acceptable excipients, wherein the epinephrine bitartrate is in an amount of 25 mg and the citric acid is in an amount of 5 mg, and wherein the citric acid, in the effective amount of epinephrine bitartrate and citric acid, is not an excipient.

5. The sublingual epinephrine tablet of claim 1, wherein at 60 minutes post-dose the effective amount of epinephrine bitartrate and citric acid maintains the blood plasma level of epinephrine in the subject above the pre-dose level of epinephrine.

6. The sublingual epinephrine tablet of claim 3, wherein at 60 minutes post-dose the effective amount of epinephrine bitartrate and citric acid maintains the blood plasma level of epinephrine in the subject above the pre-dose level of epinephrine.

7. The sublingual epinephrine tablet of claim 4, wherein at 60 minutes post-dose the effective amount of epinephrine bitartrate and citric acid maintains the blood plasma level of epinephrine in the subject above the pre-dose level of epinephrine.

\* \* \* \* \*